US009603804B2

(12) United States Patent
Uchida et al.

(10) Patent No.: US 9,603,804 B2
(45) Date of Patent: *Mar. 28, 2017

(54) SOLID PHARMACEUTICAL COMPOSITION

(71) Applicant: KYORIN PHARMACEUTICAL CO., LTD., Tokyo (JP)

(72) Inventors: Hiroshi Uchida, Tochigi (JP); Masataka Hanada, Tochigi (JP)

(73) Assignee: KYORIN PHARMACEUTICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/786,394

(22) PCT Filed: Apr. 24, 2014

(86) PCT No.: PCT/JP2014/002308
§ 371 (c)(1),
(2) Date: Oct. 22, 2015

(87) PCT Pub. No.: WO2014/174846
PCT Pub. Date: Oct. 30, 2014

(65) Prior Publication Data
US 2016/0067185 A1 Mar. 10, 2016

(30) Foreign Application Priority Data
Apr. 25, 2013 (JP) ................. 2013-092171

(51) Int. Cl.
*A61K 31/47* (2006.01)
*A61K 9/20* (2006.01)
*A61K 31/4709* (2006.01)
*B01F 3/04* (2006.01)

(52) U.S. Cl.
CPC .......... *A61K 9/2054* (2013.01); *A61K 9/2013* (2013.01); *A61K 9/2095* (2013.01); *A61K 31/4709* (2013.01); *B01F 3/04446* (2013.01)

(58) Field of Classification Search
CPC .................................................. A61K 9/2054
USPC ........................................................ 514/312
See application file for complete search history.

(56) References Cited

U.S. PATENT DOCUMENTS

| 4,822,808 | A | 4/1989 | Iida et al. |
| 4,897,270 | A | 1/1990 | Deutsch et al. |
| 5,534,534 | A | 7/1996 | Makino et al. |
| 6,727,243 | B1 | 4/2004 | Jennewein et al. |
| 2004/0082593 | A1 | 4/2004 | Sommermeyer et al. |
| 2004/0224014 | A1 | 11/2004 | Badwan et al. |
| 2005/0182052 | A1 | 8/2005 | Asahina et al. |
| 2006/0281779 | A1 | 12/2006 | Asahina et al. |
| 2008/0118564 | A1 | 5/2008 | Jerala-Strukelj et al. |

FOREIGN PATENT DOCUMENTS

| EP | 2 990 039 | 3/2016 |
| JP | 62-123118 | 6/1987 |
| JP | 62-252723 | 11/1987 |
| JP | 63-270624 | 11/1988 |
| JP | 5-194218 | 8/1993 |
| JP | 11-130674 | 5/1999 |
| JP | 2002-505290 | 2/2002 |
| JP | 2002-530338 | 9/2002 |
| JP | 2004-509921 | 4/2004 |
| JP | 2004-522782 | 7/2004 |
| JP | 2004-339198 | 12/2004 |
| JP | 2006-111639 | 4/2006 |
| JP | 2006-298811 | 11/2006 |
| JP | 2008-528456 | 7/2008 |
| WO | 90/07327 | 7/1990 |
| WO | 99/44614 | 9/1999 |
| WO | 02/067943 | 9/2002 |
| WO | 02/080013 | 10/2002 |
| WO | 03/078439 | 9/2003 |
| WO | 2005/026147 | 3/2005 |
| WO | 2006/004028 | 1/2006 |
| WO | 2006/030826 | 3/2006 |
| WO | 2006/059716 | 6/2006 |
| WO | 2013/069297 | 5/2013 |
| WO | 2013/145749 | 10/2013 |
| WO | 2013/145750 | 10/2013 |

OTHER PUBLICATIONS

Badawy et al. American Pharmacists Association J Pharm Sci 96:948-959, 2007.*
International Search Report issued Jul. 15, 2014 in International (PCT) Application No. PCT/JP2014/002308.
Hamaura et al., "Decrease in Dissolution of Cefpodoxime Proxetil Tablets by Gel Formation and Its Improvement", Journal of Pharmaceutical Science and Technology, vol. 55, No. 3, 1995, pp. 175-182.
Hamaura, "Gel formation of cefpodoxime proxetil, basic antibiotic and its formulation design", Pharm Tech Japan, vol. 17, No. 4, 2001, pp. 619-632.
Abstract of Japanese Application No. 10-245335 issued Sep. 14, 1998.
Abstract of Japanese Application No. 8-175996 issued Jul. 9, 1996.
International Preliminary Report on Patentability issued Oct. 27, 2015 in corresponding International (PCT) Application No. PCT/JP2014/002308.

(Continued)

*Primary Examiner* — Nizal Chandrakumar
(74) *Attorney, Agent, or Firm* — Wenderoth, Lind & Ponack, L.L.P.

(57) ABSTRACT

[Problem] To provide a solid pharmaceutical composition which contains a compound represented by general formula (1) or a salt thereof and suppresses decomposition of said compound or salt thereof, and a production method of said solid pharmaceutical composition.

[Solution] This solid pharmaceutical composition contains a compound represented by general formula (1) or a salt thereof, a cellulosic excipient, and an acidic substance of pH 4.0 or less.

7 Claims, 10 Drawing Sheets

(56) References Cited

OTHER PUBLICATIONS

Extended European Search Report dated Oct. 14, 2016, issued in corresponding EP Application No. 14787908.4.

* cited by examiner

SOLID PHARMACEUTICAL COMPOSITION

TECHNICAL FIELD

The present invention relates to a solid pharmaceutical composition which contains a compound represented by the general formula (1) or a salt thereof.

[Chemical Formula 1]

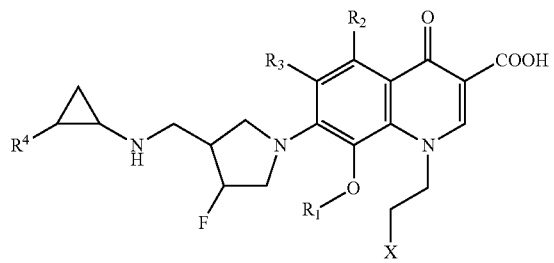

(1)

In the formula (1), $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom.

BACKGROUND ART

Although some active pharmaceutical ingredients are stable in a single solid state, changes such as strain of crystals of the active pharmaceutical ingredients are caused by pressure forming for formation of formulation, and decomposition of the active pharmaceutical ingredients in a pharmaceutical composition to be obtained is promoted (Patent Literatures 1 to 7). As conventional techniques to solve such problems, a method of adding a low-melting point oil and fat substance (Patent Literature 1), a method of adjusting the density and hardness of an uncoated tablet within specific ranges (Patent Literature 2), a method of adding a hydrophilic substance such as carrageenan (Patent Literature 3), a method of using wet granules (Patent Literature 4), a method of adding a saturated higher fatty acid and/or a saturated higher alcohol (Patent Literatures 5 and 6), a method of adding a sucrose fatty acid ester (Patent Literature 7), a method of adding minute gelatin spheres and/or gelatin foams (Patent Literature 8), and a method of using a monosaccharide alcohol (Patent Literatures 9 and 10) have been known.

On the other hand, some active pharmaceutical ingredients which cause gelling under a certain condition have been known (Patent Literatures 11 to 17 and Non-Patent Literatures 1 and 2). As a formulation which contains a quinolone carboxylic acid antimicrobial agent in which a main drug is stabilized, an oral composition which contains an acidic additive (Patent Literature 18) and an injection formulation which contains an acidic additive (Patent Literatures 19 and 20) have been known.

CITATION LIST

Patent Literature

Patent Literature 1: JPH05-194218
Patent Literature 2: JP2006-111639
Patent Literature 3: JP2008-528465
Patent Literature 4: JPH10-245335
Patent Literature 5: JPS62-252723
Patent Literature 6: JPS63-270624
Patent Literature 7: JPH08-175996
Patent Literature 8: WO1990/007327 Pamphlet
Patent Literature 9: WO2002/080013 Pamphlet
Patent Literature 10: JPH11-130674
Patent Literature 11: JP2006-298811
Patent Literature 12: WO2006/030826
Patent Literature 13: JP2002-505290
Patent Literature 14: JP2004-522782
Patent Literature 15: JPS62-123118
Patent Literature 16: WO2006/059716
Patent Literature 17: JP2002-530338
Patent Literature 18: JP2004-339198
Patent Literature 19: JP2004-509921
Patent Literature 20: WO2006/004028

Non-Patent Literature

Non-Patent Literature 1: Journal of Pharmaceutical Science and Technology, Japan, Vol. 55, No. 3 (1995), pp. 175-182
Non-Patent Literature 2: PharmTech Japan, vol. 17, No. 4 (2001) 87-100 (619-632).

SUMMARY OF INVENTION

Technical Problem

The present invention provides a novel pharmaceutical composition which can suppress decomposition of a compound represented by the following general formula (1) (hereinafter also referred to as a compound of the formula (1)) or a salt thereof to be contained and a method of producing the same.

[Chemical Formula 2]

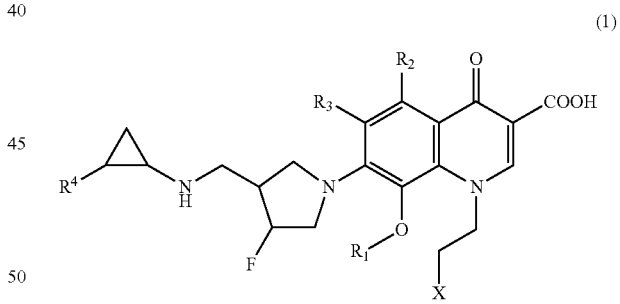

(1)

In the formula (1), $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom.

Solution to Problem

The present inventors have studied formulation of a pharmaceutical composition which can suppress decomposition of the compound of the formula (1) to be contained. During the study, it has been made clear that a cyclopropylaminomethyl structure contained in the compound of the formula (1) is likely to chemically decomposed, and a compound represented by the general formula (2) (hereinafter referred to as the compound of the formula (2)) in which a cyclopropyl group is eliminated is generated by pressure forming, for example, dry granulation or the like.

[Chemical Formula 3]

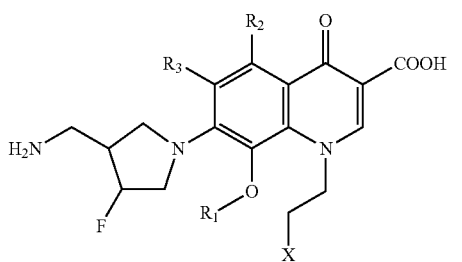

(2)

In the formula (2), $R^1$, $R^2$, $R^3$, and X are the same as the above-described definitions.

The inventors have intensively investigated, and as a result found that when a composition which contains the compound of the formula (1) or a salt thereof, a cellulosic excipient, and a predetermined acidic substance is formed, chemical decomposition of the compound of the formula (1) into, for example, the compound of the formula (2) or the like can be suppressed. Thus, the present invention has been completed.

The summary of the present invention is as follows:

[1] A solid pharmaceutical composition, containing a compound represented by the general formula (1):

[Chemical Formula 4]

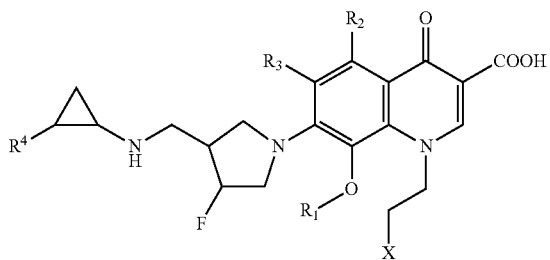

(1)

(wherein $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom) or a salt thereof, a cellulosic excipient, and an acidic substance of pH 4.0 or lower.

[2] The solid pharmaceutical composition according to [1], including, as the acidic substance, one or two or more kinds of compounds selected from the group consisting of glutamic acid hydrochloride, tartaric acid, citric acid, malic acid, fumaric acid, monobasic sodium citrate, glutamic acid, aspartic acid, and alginic acid.

[3] The solid pharmaceutical composition according to [1], wherein the acidic substance has a solubility in water at 20° C. of 30% or less.

[4] The solid pharmaceutical composition according to [1] or [3], wherein the acidic substance has a pH of 2.2 or higher and 4.0 or lower.

[5] The solid pharmaceutical composition according to [1], including, as the acidic substance, one or two or more kinds of compounds selected from the group consisting of fumaric acid, monobasic sodium citrate, glutamic acid, aspartic acid, and alginic acid.

[6] The solid pharmaceutical composition according to anyone of [1] to [5], wherein the cellulosic excipient is crystalline cellulose.

[7] The solid pharmaceutical composition according to anyone of [1] to [6], wherein the solid pharmaceutical composition contains a hydrochloride of the compound represented by the formula (1) as the compound represented by the formula (1) or salt thereof.

[8] The solid pharmaceutical composition according to [1], obtained by mixing the compound represented by the formula (1) or salt thereof, the cellulosic excipient, and the acidic substance and granulating the obtained mixture through a dry granulation method.

[9] A method of producing a solid pharmaceutical composition, including:

mixing a compound represented by the general formula (1):

[Chemical Formula 5]

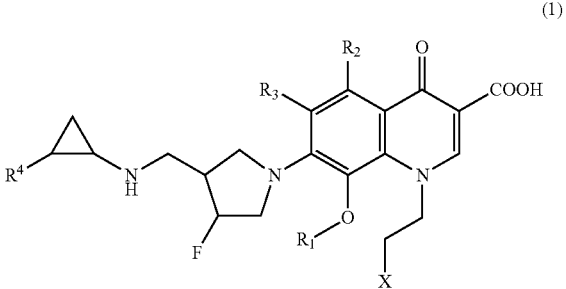

(1)

(wherein $R^1$ represents an alkyl group having 1 to 3 carbon atoms of which one or two or more hydrogen atoms may be substituted with a halogen atom, an amino group, or a cyano group, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom) or a salt thereof, a cellulosic excipient, and an acidic substance of pH 4.0 or lower; and granulating the obtained mixture through a dry granulation method.

Advantageous Effects of Invention

The present invention can provide a novel composition which can suppress decomposition of the compound of the formula (1) or salt thereof to be contained and a method of producing the same.

Figure 2:
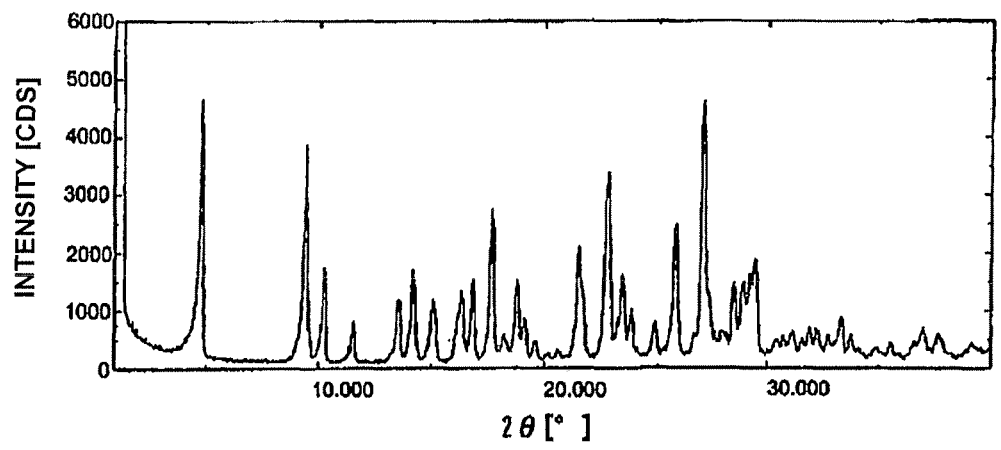

FIG. 2 is an X-ray powder diffraction pattern of 7-[(3S,4S)-3-{(cyclopropylamino)methyl}-4-fluoropyrolidin-1-yl}-6-fluoro-1-(2-fluoroethyl)-8-methoxy-4-oxo-1,4-dihydroquinoline-3-carboxylic acid hydrochloride hydrate (B-type crystal).

Figure 3:
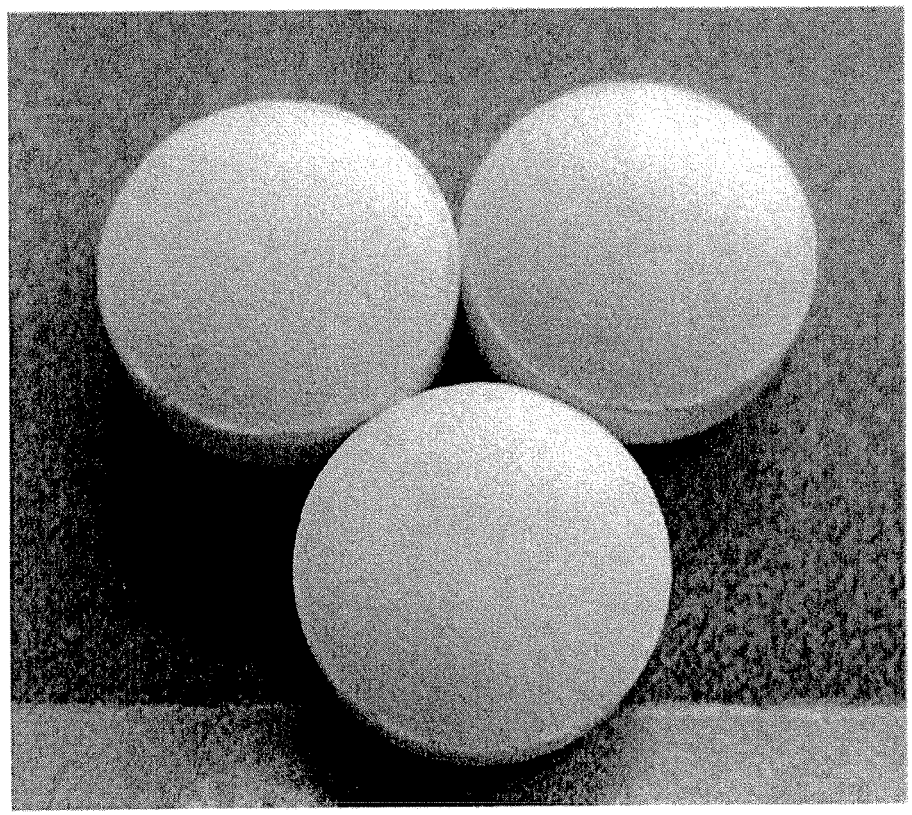

FIG. 3 is a photograph of a tablet obtained in Example 1 immediately after production.

Figure 4:
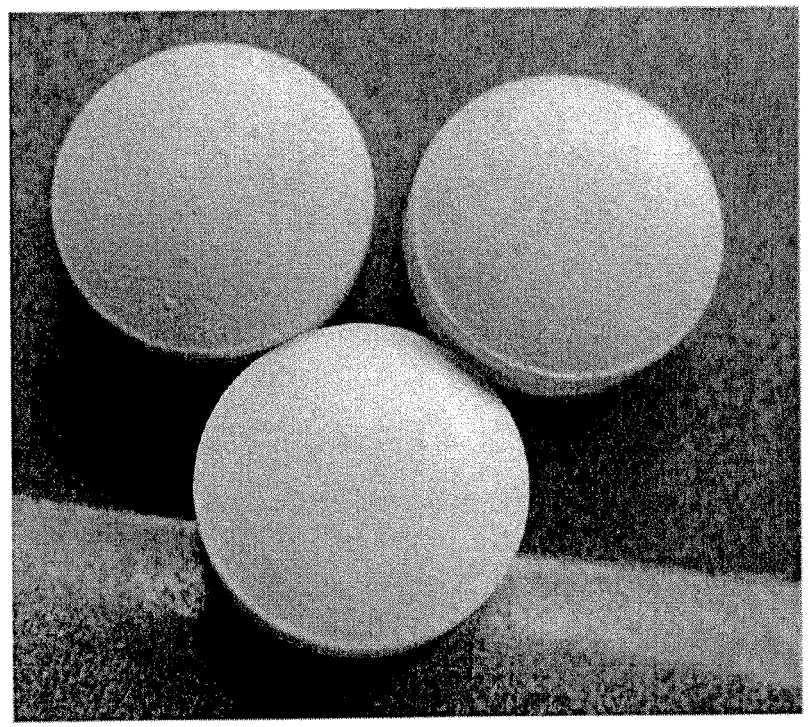

FIG. 4 is a photograph of a tablet obtained in Example 2 immediately after production.

Figure 5:

FIG. 5 is a photograph of a tablet obtained in Example 3 immediately after production.

Figure 6:
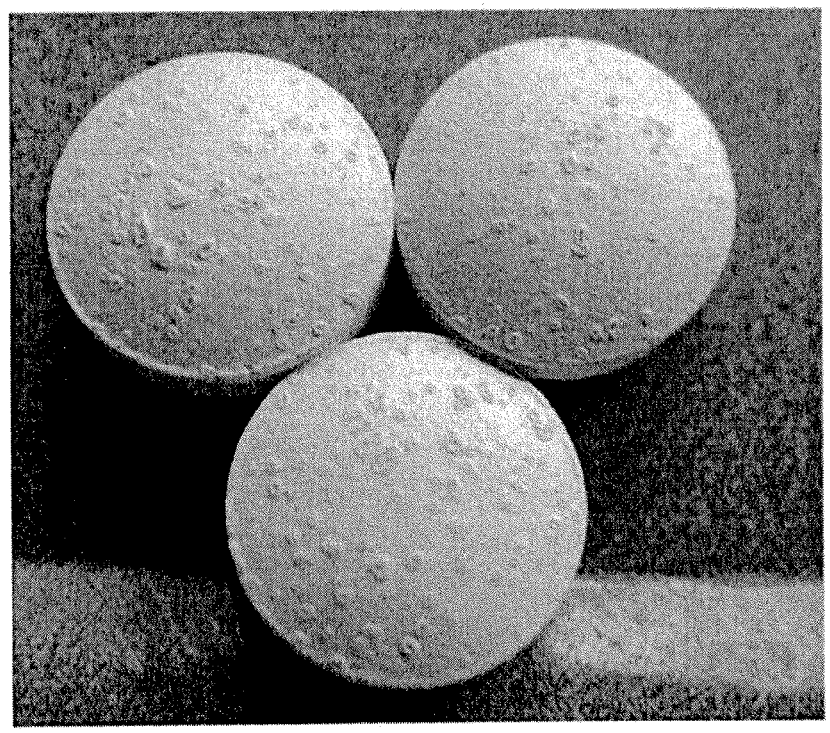

FIG. 6 is a photograph of a tablet obtained in Example 4 immediately after production.

Figure 7:
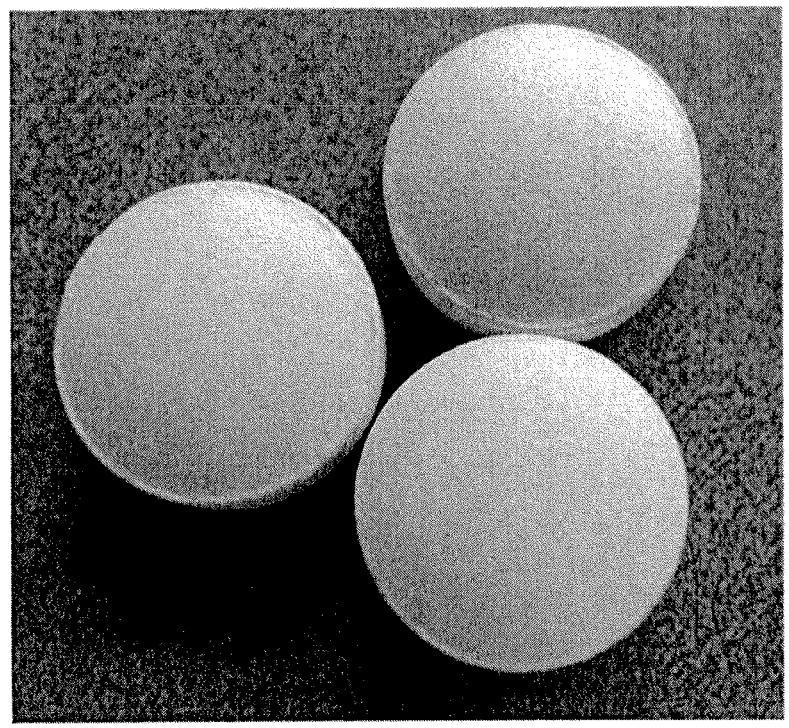

FIG. 7 is a photograph of a tablet obtained in Example 5 immediately after production.

Figure 8:
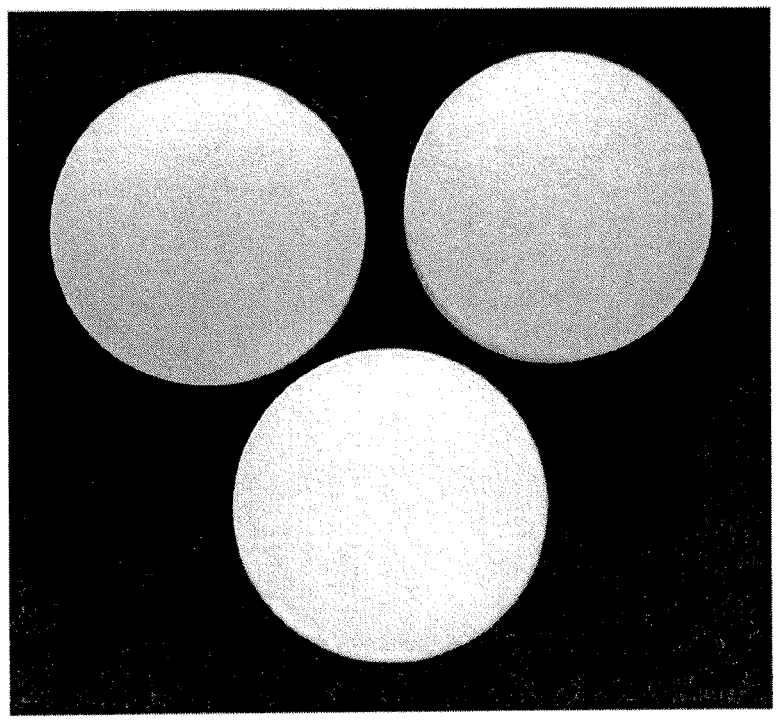

FIG. 8 is a photograph of a tablet obtained in Example 6 immediately after production.

Figure 9:
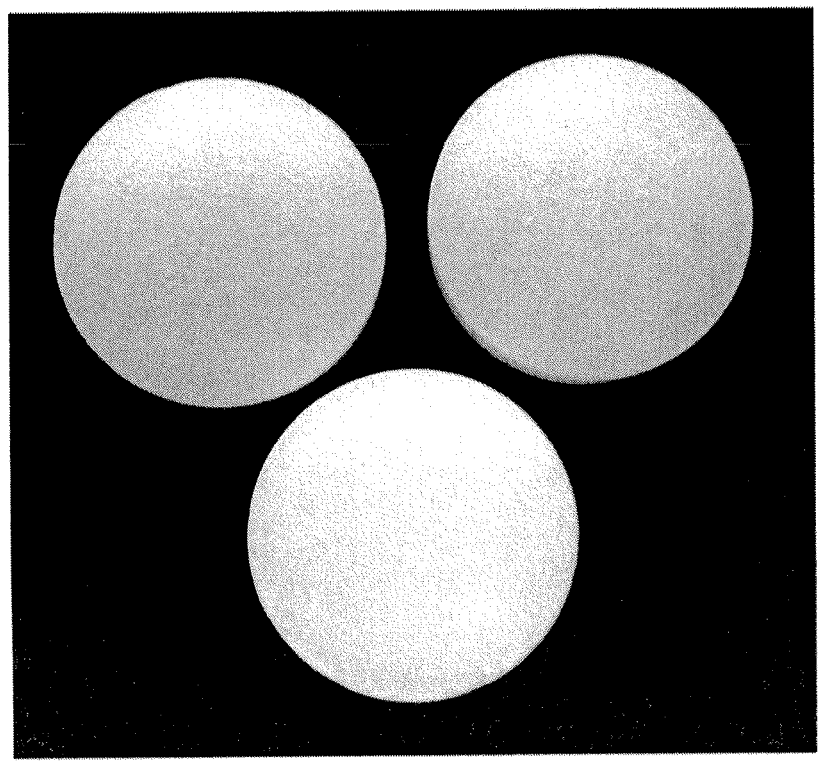

FIG. 9 is a photograph of a tablet obtained in Example 7 immediately after production.

Figure 10:
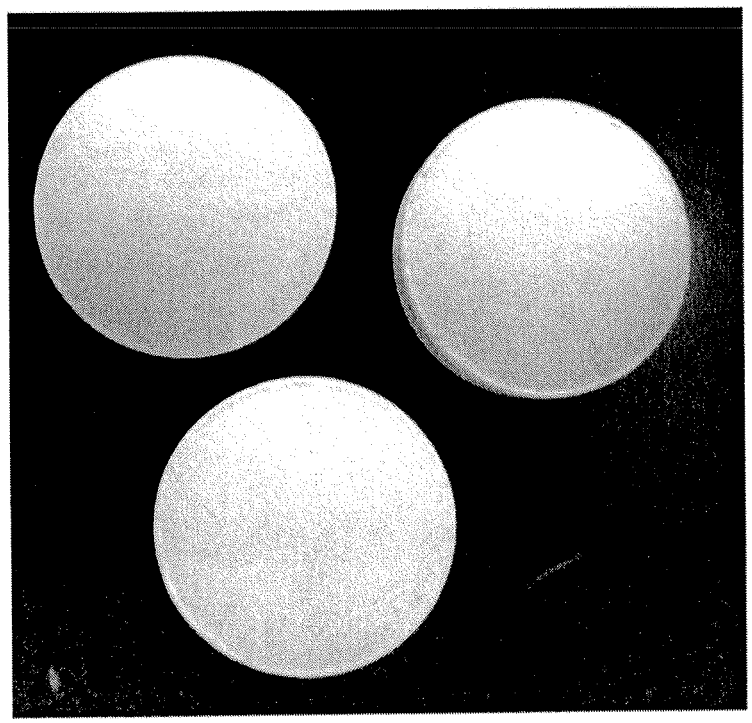

FIG. 10 is a photograph of a tablet obtained in Example 8 immediately after production.

Figure 11:
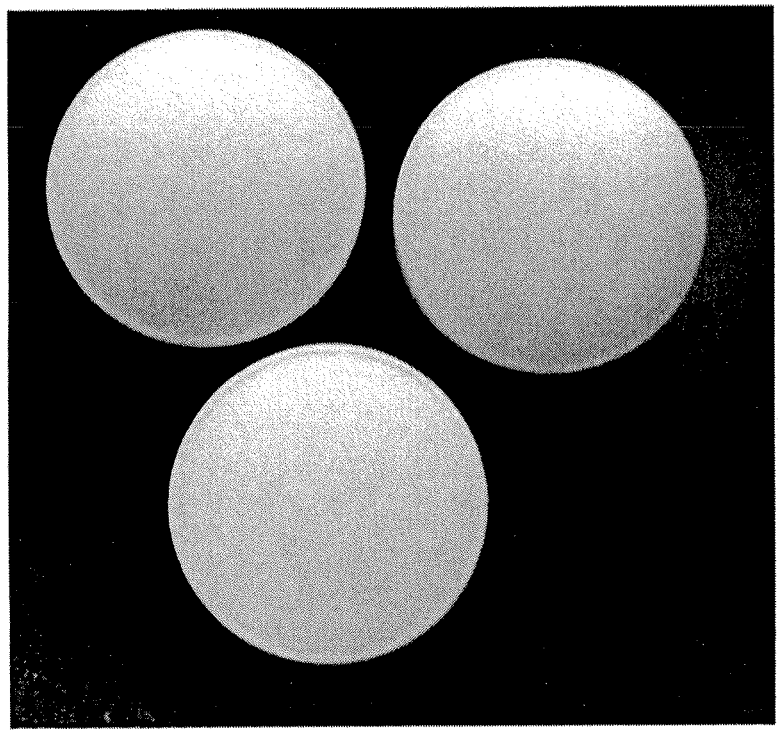

FIG. 11 is a photograph of a tablet obtained in Example 9 immediately after production.

Figure 12:
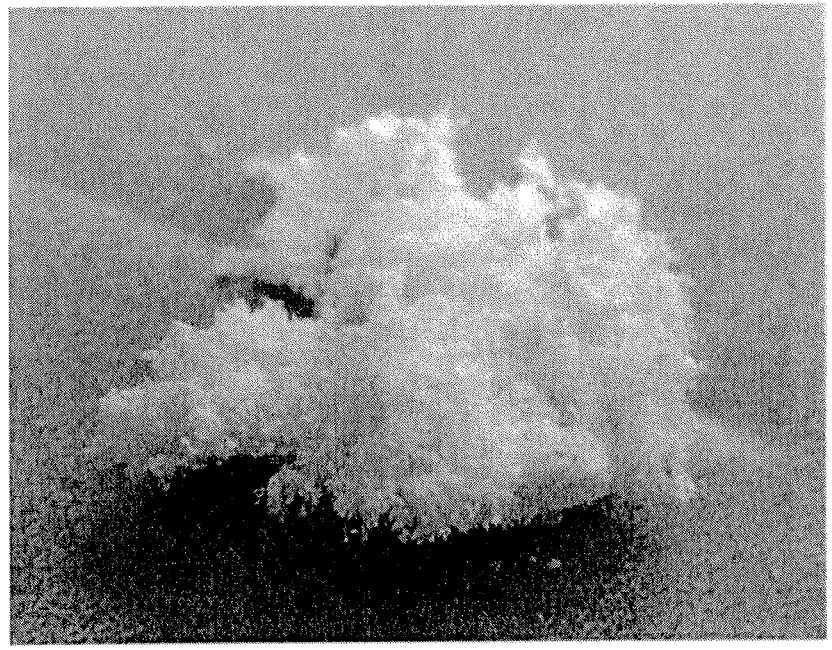

FIG. 12 is a photograph of the tablet obtained in Example 1 after storage under conditions of 60° C. and 90% RH for 2 weeks.

Figure 13:
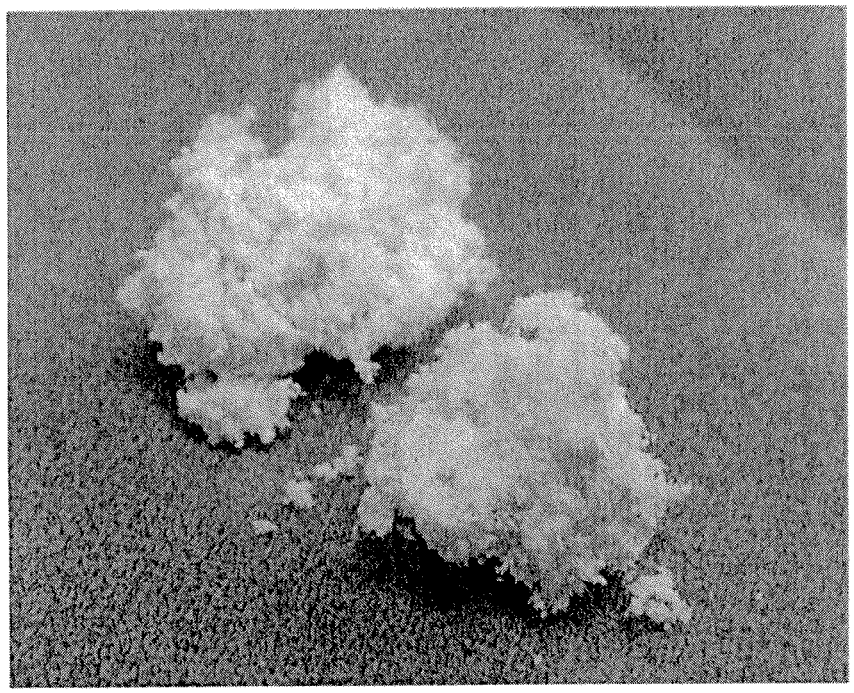

FIG. 13 is a photograph of the tablet obtained in Example 2 after storage under conditions of 60° C. and 90% RH for 2 weeks.

Figure 14:
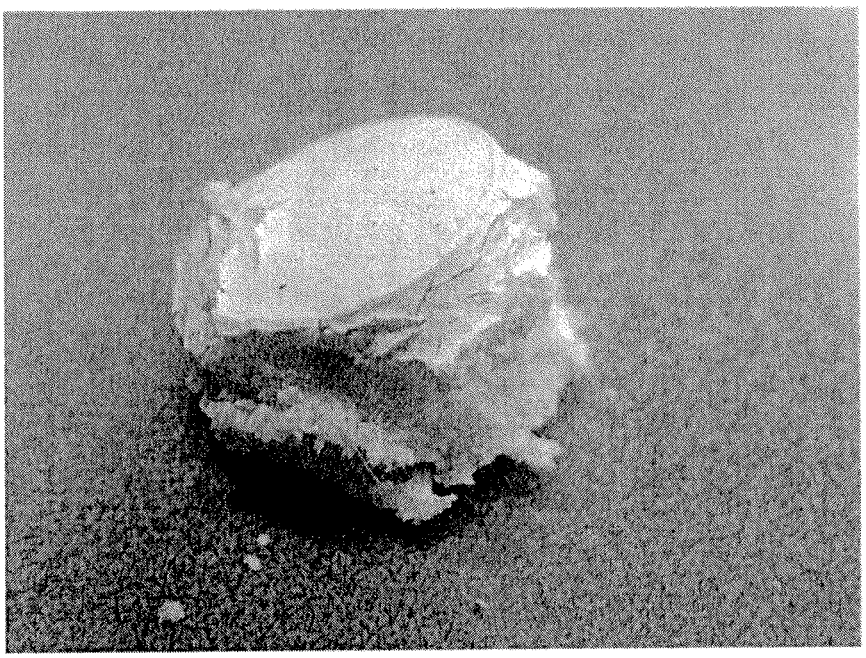

FIG. 14 is a photograph of the tablet obtained in Example 3 after storage under conditions of 60° C. and 90% RH for 2 weeks.

Figure 15:
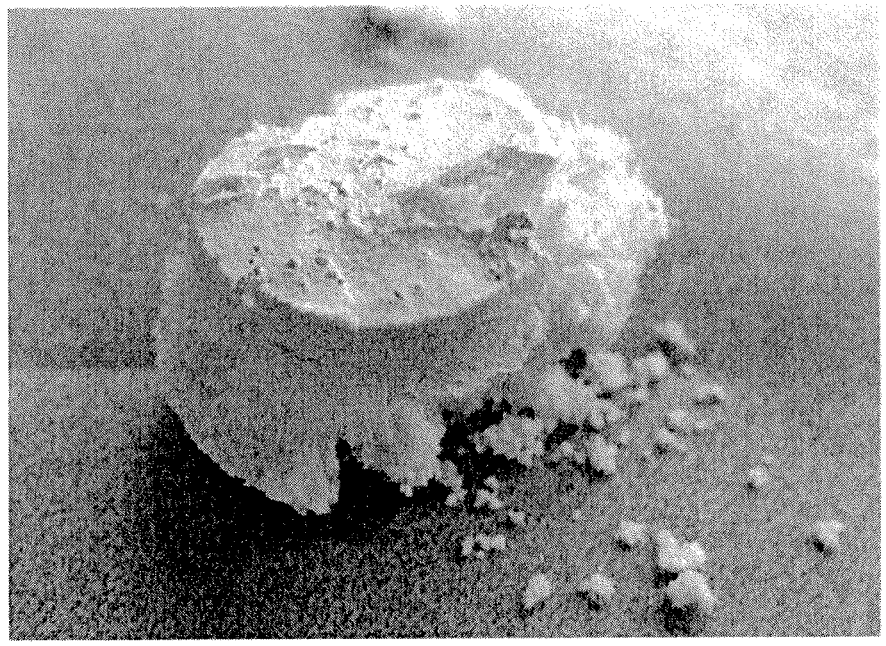

FIG. 15 is a photograph of the tablet obtained in Example 4 after storage under conditions of 60° C. and 90% RH for 2 weeks.

Figure 16:
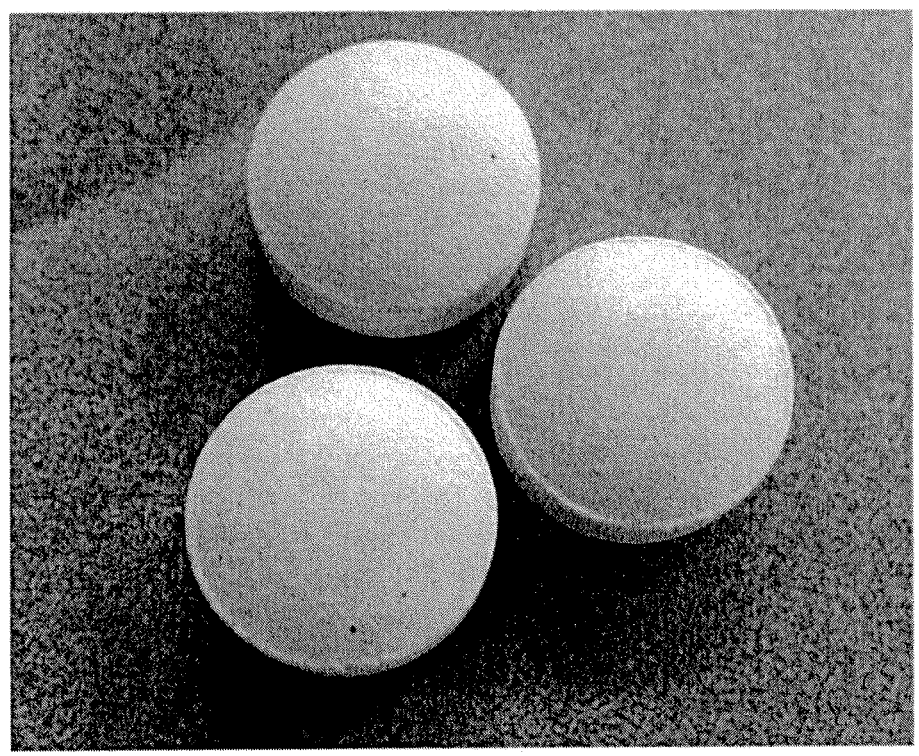

FIG. 16 is a photograph of the tablet obtained in Example 5 after storage under conditions of 60° C. and 90% RH for 2 weeks.

Figure 17:
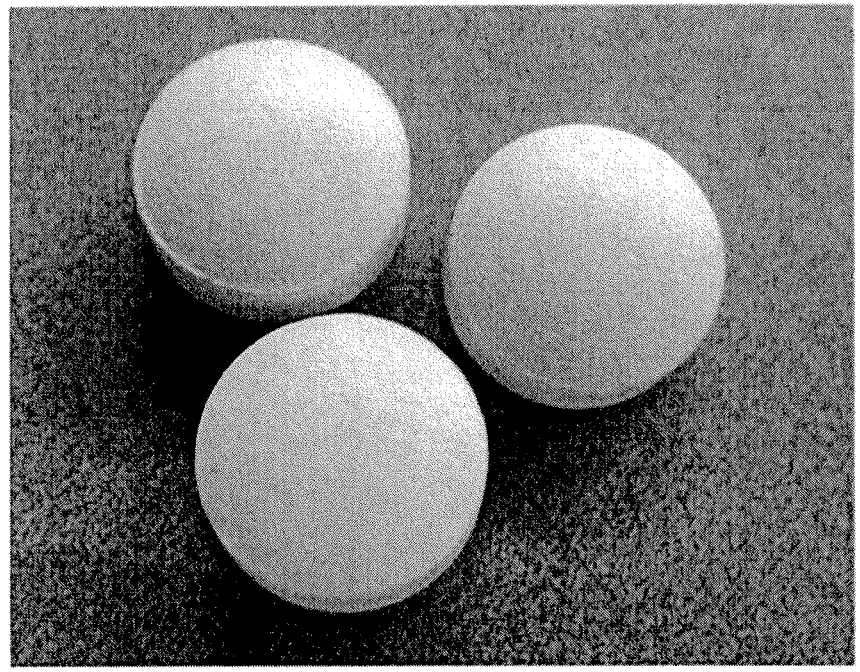

FIG. 17 is a photograph of the tablet obtained in Example 6 after storage under conditions of 60° C. and 90% RH for 2 weeks.

Figure 18:
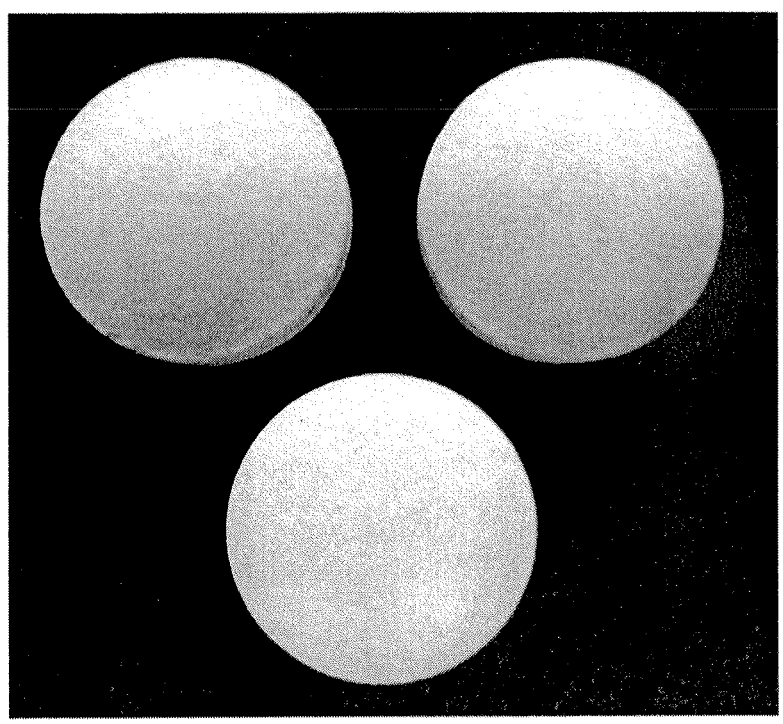

FIG. 18 is a photograph of the tablet obtained in Example 7 after storage under conditions of 60° C. and 90% RH for 2 weeks.

Figure 19:
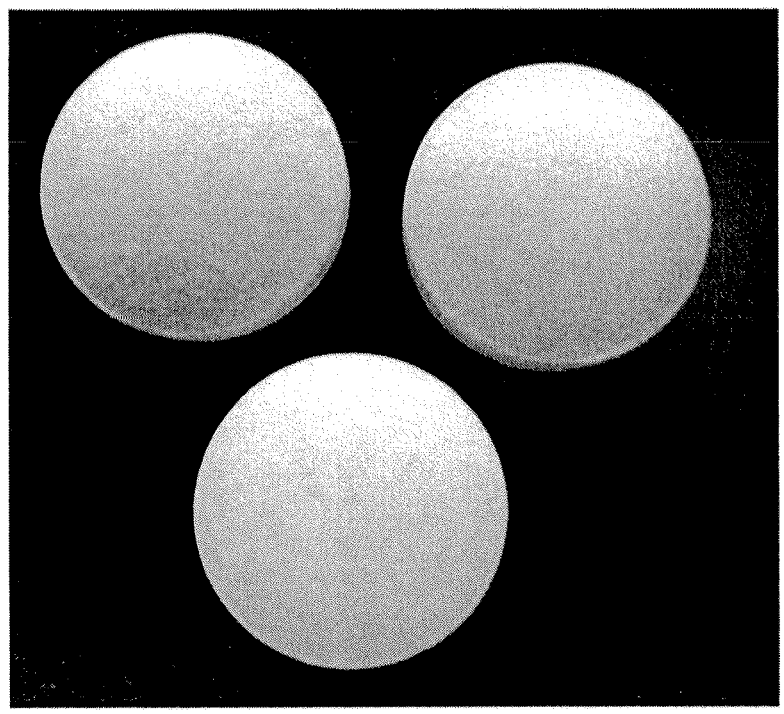

FIG. 19 is a photograph of the tablet obtained in Example 9 after storage under conditions of 60° C. and 90% RH for 2 weeks.

Figure 20:
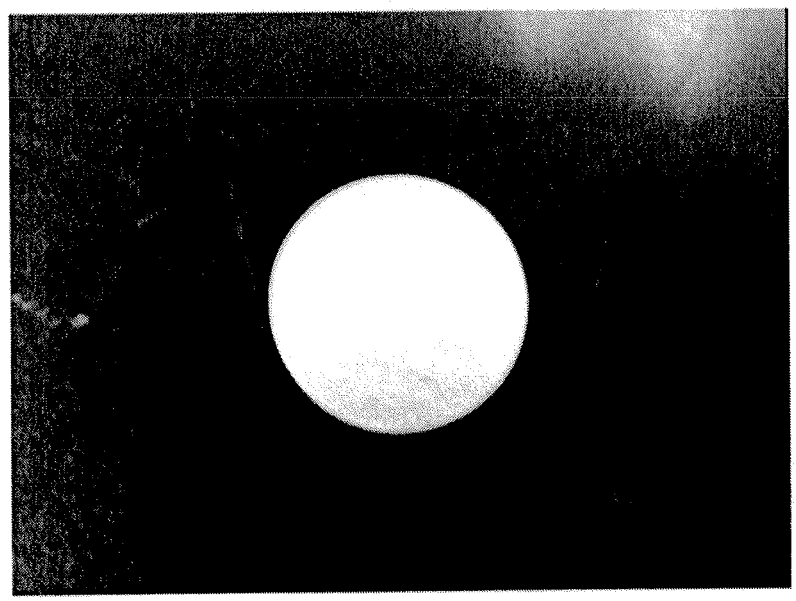

FIG. 20 is a photograph of the tablet obtained in Example 11 after storage under conditions of 60° C. and 90% RH for 2 weeks.

DESCRIPTION OF EMBODIMENTS

Hereinafter, one of embodiments of the present invention will be described in detail.

The embodiment relates to a solid pharmaceutical composition which contains at least a compound represented by the general formula (1) or a salt thereof, a cellulosic excipient, and an acidic substance of pH 4.0 or lower.

The solid pharmaceutical composition herein represents a pharmaceutical composition including a solid component to be contained.

[Chemical Formula 6]

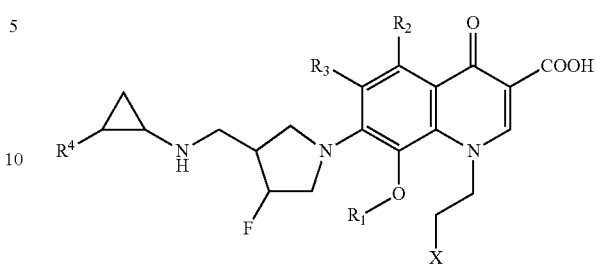

(1)

In the formula (1), $R^1$ represents an alkyl group having 1 to 3 carbon atoms, $R^2$ represents an alkyl group having 1 to 3 carbon atoms, a hydrogen atom, a halogen atom, a hydroxyl group, or an amino group, $R^3$ represents a hydrogen atom or a halogen atom, $R^4$ represents a hydrogen atom or a fluorine atom, and X represents a halogen atom. One or two or more hydrogen atoms of the alkyl group having 1 to 3 carbon atoms represented by $R^1$ may be substituted with a halogen atom, an amino group, or a cyano group.

The "halogen atom" described herein represents a fluorine atom, a chlorine atom, a bromine atom, or an iodine atom. In the general formula (1), the halogen atom is preferably a fluorine atom. The "alkyl group having 1 to 3 carbon atoms" described herein is a methyl group, an ethyl group, a propyl group, or a 2-propyl group.

The compound of the formula (1) or salt thereof in the solid pharmaceutical composition of this embodiment can be produced, for example, through a method described in WO2005/026147 pamphlet. The compound of the formula (1) contained in the solid pharmaceutical composition of this embodiment is preferably 7-[3-{(cyclopropylamino)methyl}-4-fluoropyrrolidin-1-yl]-6-fluoro-1-(2-fluoroethyl)-8-methoxy-4-oxo-1,4-dihydroquinoline-3-carboxylic acid, and more preferably 7-[(3S,4S)-3-{(cyclopropylamino)methyl}-4-fluoropyrrolidin-1-yl]-6-fluoro-1-(2-fluoroethyl)-8-methoxy-4-oxo-1,4-dihydroquinoline-3-carboxylic acid.

It is preferable that the solid pharmaceutical composition of this embodiment contain a salt of the compound of the formula (1) from the viewpoint of improvement in solubility in water.

The salt of the compound of the formula (1) to be contained in the solid pharmaceutical composition of this embodiment is not particularly limited so long as it is a pharmaceutically acceptable salt. Examples of the salt of the compound of the formula (1) may include salts with inorganic acids such as hydrochoric acid, hydrobromic acid, sulfuric acid, and phosphoric acid, salts with organic acids such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and salts with metals such as sodium, potassium, magnesium, calcium, aluminum, cesium, chromium, cobalt, copper, iron, zinc, platinum, and silver. Among these, a hydrochloride is particularly preferred from the viewpoint of stability. A hydrochloride of the compound of the formula (1) is excellent since decomposition of the compound due to light irradiation is unlikely to proceed and the degree of chemical decomposition is low even in storage under an acceleration test condition as compared with the compound of the formula (1) in a free form and another salt of the compound of the formula (1).

The salt of the compound of the formula (1) to be contained in the solid pharmaceutical composition of this embodiment is preferably 7-[3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride, and more preferably 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride.

The solid pharmaceutical composition of this embodiment contains the compound of the formula (1) or salt thereof, a cellulosic excipient, and an acidic substance of pH 4.0 or lower.

The "cellulosic excipient" described herein is an excipient which contains cellulose or derivatives thereof as a component. As the cellulosic excipient, the solid pharmaceutical composition of this embodiment contains one or two or more kinds of crystalline cellulose, carmellose, carmellose calcium, carmellose sodium, croscarmellose sodium, carboxymethyl cellulose calcium, and low substituted hydroxypropylcellulose. Among these, it is preferable that the cellulosic excipient in the solid pharmaceutical composition of this embodiment be crystalline cellulose since the hardness of molded tablet is high.

The "acidic substance" described herein is a substance which is dissolved in water to generate hydrogen ions. From the viewpoint of suppressing production of the compound of the formula (2) or the like, the solid pharmaceutical composition of the embodiment contains an acidic substance of pH 4.0 or lower. Examples of the acidic substance of pH 4.0 or lower may include polyvalent carboxylic acids, and specific examples thereof may include inorganic acid salts of amino polyvalent carboxylic acids such as glutamic acid hydrochloride, hydroxy polyvalent carboxylic acids such as tartaric acid, citric acid, and malic acid, saturated polyvalent carboxylic acids such as adipic acid and succinic acid, unsaturated polyvalent carboxylic acid such as fumaric acid, amino polyvalent carboxylic acid such as glutamic acid and aspartic acid, acidic polysaccharides such as alginic acid, alkali metal salts of hydroxy polyvalent carboxylic acids such as monobasic sodium citrate, and polymeric polyvalent carboxylic acids such as a methacrylic acid copolymer L. In the solid pharmaceutical composition of the embodiment, for example, one or two or more kinds of acidic substances among these can be used. It is preferable that the contained acidic substance of pH 4.0 or lower be an acidic substance of pH 2.2 or higher and 4.0 or lower from the viewpoint of suppressing decomposition of the compound of the formula (1) or salt thereof and a change of appearance of the solid pharmaceutical composition of this embodiment. Examples of the acidic substance of pH 2.2 or higher and 4.0 or lower may include saturated polyvalent carboxylic acids such as adipic acid and succinic acid, unsaturated polyvalent carboxylic acids such as fumaric acid, amino polyvalent carboxylic acids such as glutamic acid and aspartic acid, acidic polysaccharides such as alginic acid, alkali metal salts of hydroxy polyvalent carboxylic acids such as monobasic sodium citrate, and polymeric polyvalent carboxylic acids such as a methacrylic acid copolymer L.

"pH" described herein is a value obtained by measuring the pH of liquid (concentration: 2.5%), in which 50 mg of object substance is weighed, and dissolved or suspended in 1,950 μL of water, with a pH meter.

From the viewpoint of further suppressing production of the compound of the formula (2) or the like, it is preferable that the content of the acidic substance (when two or more kinds of acidic substances of pH 4.0 or lower are contained, the total amount thereof is used) in the solid pharmaceutical composition of this embodiment be 0.05 parts by mass or more and 0.50 parts by mass or less relative to 1 part by mass of the compound of the formula (1) or salt thereof. The content of the acidic substance of pH 4.0 or lower in the solid pharmaceutical composition of this embodiment is more preferably 0.05 parts by mass or more and 0.40 parts by mass or more relative to 1 part by mass of the compound of the formula (1) or salt thereof, further preferably 0.10 parts by mass or more and 0.30 parts by mass or more, and still further preferably 0.15 parts by mass or more and 0.30 parts by mass or more.

When the solid pharmaceutical composition of this embodiment is prepared, for example, as a tablet in which an uncoated tablet is coated with a coating, the acidic substance existing in the vicinity of a surface may be dissolved in a moisture in the coating solution to generate mottles (irregularities) on the surface of the solid pharmaceutical composition. The mottles give bad appearance, and the compliance of a patient who should take a pharmaceutical composition may be deteriorated. Therefore, it is not preferred. From the viewpoint of enabling to suppress the decomposition of the compound of the formula (1) or salt thereof as well as suppress a phenomenon in which mottles are observed on the surface of the solid pharmaceutical composition of this embodiment, it is preferable that the solid pharmaceutical composition of this embodiment contain one or two more kinds of acidic substances of pH 4.0 or lower selected from inorganic acid salts of amino polyvalent carboxylic acids such as glutamic acid hydrochloride, saturated polyvalent carboxylic acids such as adipic acid and succinic acid, unsaturated polyvalent carboxylic acids such as fumaric acid, amino polyvalent carboxylic acids such as glutamic acid and aspartic acid, acidic polysaccharides such as alginic acid, alkali metal salts of hydroxy polyvalent carboxylic acids such as monobasic sodium citrate, and polymeric polyvalent carboxylic acids such as a methacrylic acid copolymer L.

From the viewpoint of enabling to suppress the phenomenon in which mottles are observed on the surface of the solid pharmaceutical composition, it is more preferable to use an acidic substance having a solubility in water at 20° C. of 30% or less as an acidic substance contained in the solid pharmaceutical composition of this embodiment. Examples of the acidic substance having a solubility in water at 20° C. of 30% or less may include L-glutamic acid hydrochloride, monobasic sodium citrate, adipic acid, succinic acid, fumaric acid, L-glutamic acid, L-aspartic acid, and alginic acid. Among these, it is particularly preferable that the acidic substance to be contained in this embodiment be alginic acid since alginic acid is hardly dissolved in water.

The "solubility in water" herein is a value obtained by calculation using the following equation (A) on the basis of the mass (g) of a solute that is dissolved in 100 g of water.

$$MW=\{C/(100+C)\}\times 100 \tag{A}$$

In the equation (A), MW represents the solubility (%) in water and C represents the mass (g) of a solute that is dissolved in 100 g of water.

Examples of the solid pharmaceutical composition of this embodiment may include an oral composition. In particular, when a component which contains the compound of the formula (1) or salt thereof is formed into a dosage form produced through a pressing process such as compression molding and pressing into tablets, techniques according to this embodiment can be suitably applied. Specifically, the solid pharmaceutical composition of this embodiment can be formed into a solid oral preparation such as a tablet, a granule (subtle granule), a capsule, and a powder, and preferably, can be formed into a tablet.

The ratio of each component in the solid pharmaceutical composition of this embodiment is not particularly limited, and can be appropriately selected according to the dosage form or the like by those skilled in the art.

For example, when the solid pharmaceutical composition of this embodiment is prepared as a tablet, the content of the compound of the formula (1) or salt thereof is preferably 10% by mass or more and 70% by mass or less relative to the whole mass of uncoated tablet, more preferably 20% by mass or more and 60% by mass or less, particularly preferably 30% by mass or more and 50% by mass or less, and further preferably 35% by mass or more and 45% by mass or less, for example, 43% by mass.

The content of the cellulosic excipient in the solid pharmaceutical composition of this embodiment is 10% by mass or more and 70% by mass or less relative to the whole mass of uncoated tablet, more preferably 20% by mass or more and 60% by mass or less, particularly preferably 25% by mass or more and 50% by mass or less, and further preferably 30% by mass or more and 40% by mass or less, for example, 34% by mass or 37% by mass.

From the viewpoint of suppressing the phenomenon in which mottles on the surface of the solid pharmaceutical composition of this embodiment is observed, the content of the acidic substance of pH 4.0 or lower (when two or more kinds of acidic substances are used, the total content thereof is applied) is 5% by mass or more and 20% by mass or less relative to the whole mass of uncoated tablet, and preferably 7% by mass or more and 15% by mass or less.

The "uncoated tablet" described herein means a tablet which is obtained by pressing a raw material into a tablet and is a state before applying a coating.

The solid pharmaceutical composition of this embodiment can be produced in accordance with a common method corresponding to the dosage form, and the producing method can be appropriately selected by those skilled in the art.

When the solid pharmaceutical composition of this embodiment is subjected to a granulation process for production, it is preferable that the granulation be in accordance with a dry granulation method. The "dry granulation method" described herein is a method in which a raw material powder is compression-molded, crushed, and classified into particles having appropriate size. According to the dry granulation method, granulation can be carried out without use of water. Therefore, the gelling of the compound of the formula (1) or salt thereof due to effects of water can be suppressed.

Hereinafter, the content of the solid pharmaceutical composition of this embodiment will be described more specifically with reference to one example of a method of producing the solid pharmaceutical composition of this embodiment as a tablet, and the scope of the present invention is not limited thereby.

(General Production Method)
1. A, B, and C components described below are mixed. To the powder obtained by the mixing, a lubricant such as stearic acid, a stearic acid salt (a salt with metal such as aluminum, potassium, sodium, calcium, and magnesium), and sodium laurylsulfate may be further added.

A component: a compound represented by the formula (1) or a salt thereof

B component: one or two or more kinds of cellulosic excipients selected from the group consisting of crystalline cellulose, carmellose, carmellose calcium, carmellose sodium, croscarmellose sodium, carboxymethyl cellulose calcium, and low substituted hydroxypropylcellulose C component: one or two or more kinds of acidic substances selected from the group consisting of inorganic acid salts of amino polyvalent carboxylic acids such as glutamic acid hydrochloride, hydroxy polyvalent carboxylic acids such as tartaric acid, citric acid, and malic acid, saturated polyvalent carboxylic acids such as adipic acid and succinic acid, unsaturated polyvalent carboxylic acids such as fumaric acid, amino polyvalent carboxylic acids such as glutamic acid and aspartic acid, acidic polysaccharides such as alginic acid, alkali metal salts of hydroxy polyvalent carboxylic acids such as monobasic sodium citrate, and polymeric polyvalent carboxylic acids such as a methacrylic acid copolymer L 2. Granulation is performed, for example, in accordance with a dry granulation method. Specifically, the resultant mixture is compression-molded by a compression molding device such as a roller compactor or a tableting machine (slug machine), crushed and subjected to size adjustment by a particle sizing device such as a roll granulator or a sieve, to obtain a granulated substance. To the granulated substance, a cellulosic excipient such as crystalline cellulose, carmellose, carmellose calcium, carmellose sodium, croscarmellose sodium, carboxymethyl cellulose calcium, and low substituted hydroxypropylcellulose can also be added, and a disintegrant such as low substituted hydroxypropylcellulose, crystalline cellulose, hydroxypropyl starch, carmellose, carmellose calcium, carmellose sodium, potato starch, corn starch, low substituted hydroxypropylcellulose, crospovidone, croscarmellose sodium, and sodium carboxymethyl starch can also be added. To the granulated substance, a lubricant such as stearic acid, a stearic acid salt (a salt with metal such as aluminum, calcium, sodium, potassium, and magnesium), and sodium laurylsulfate can be added.

3. From the resulting granulated substance or a mixture of the granulated substance and an additive, a tablet (uncoated tablet) is obtained by pressing with a tableting machine. After the pressing into tablets, the resulting uncoated tablet may be coated with a coating agent such as hypromellose and Kollicoat IR.

EXAMPLES

Hereinafter, the present invention will be described in more detail with reference to Examples. Examples are not intended to limit the scope of the present invention.

In the following Examples, an NMR spectrum was determined with JEOL JNM-EX400 nuclear magnetic resonance spectrometer using tetramethylsilane (TMS) as an internal standard. AMS spectrum was determined with JEOL JMS-T100LP and JMS-SX102A mass spectrometers. Elementary analysis was carried out with YANACO CHN CORDER MT-6 analyzer.

Reference Example 1

Bis(acetato-O)-[6,7-difluoro-1-(2-fluoroethyl)-8-methoxy-4-oxo-1,4-dihydroquinoline-3-carboxylato-$O^3,O^4$]boron 103 g (1.67 mol) of boric acid (for formation of catalyst) was added to 21.4 L (225 mol) of acetic anhydride under a nitrogen atmosphere, and the mixture was heated and stirred at 70.0 to 76.9° C. for 30 minutes (at a stirring rate of 69.5 rpm). The mixture was cooled to an inner temperature of 24.6° C., 1.01 kg (16.3 mol) of first additional boric acid was added, and the mixture was stirred at 24.6 to 27.4° C. for 30 minutes. 1.01 kg (16.3 mol) of second additional boric acid was added, and the mixture was stirred at 24.7 to 27.5° C. for 30 minutes. 1.01 kg (16.3 mol) of third additional boric acid was added, and the mixture was stirred at 24.7 to 27.7° C. for 30 minutes. 1.01 kg (16.3 mol) of fourth additional boric acid was added, and the mixture was stirred at 25.4 to 29.4° C. for 30 minutes. The mixture was further stirred at 50.0 to 56.9° C. for 30 minutes, to prepare a boric acid triacetate adjustment liquid. To the adjustment liquid, 5.50 kg (16.7 mol) of 6,7-difluoro-1-(2-fluoroethyl)-8-methoxy-4-oxo-1,4-dihydroquinoline-3-carboxylic acid ethyl ester was added, and the mixed liquid was stirred at 54.7 to 56.9° C. for 3 hours. The mixed liquid was cooled to 30.0° C., and allowed to stand at room temperature overnight. The mixed liquid was heated to 58.6° C. to dissolve the deposited compound, and 16.5 L of acetone was added to the mixed liquid to obtain a reaction liquid (a).

A mixed liquid of 193 L of water and 33.7 L (555 mol) of ammonia water (28%) was cooled to −0.6° C. under a nitrogen atmosphere. To the mixed liquid, the reaction liquid (a) was added, and the mixture was washed with 11.0 L of acetone. The mixture was cooled to 15.0° C., and stirred at 4.3 to 15.0° C. for 1 hour. The deposited crystal was collected by filtration, and the collected crystal was washed with 55.0 L of water to obtain 14.1 kg of crude wet crystal. The crude wet crystal was dried under reduced pressure at a setting temperature of 65.0° C. for about 22 hours to obtain 6.93 kg of crude crystal (yield: 96.7%).

To the crude crystal obtained, 34.7 L of acetone was added under a nitrogen atmosphere, and the mixture was heated (at hot water setting temperature of 57.0° C.) to dissolve the crude crystal. During the heating, 69.3 L of diisopropyl ether was added dropwise (added amount: 12.0 L) until crystallization. After confirmation of crystallization, the mixture was stirred at 48.3 to 51.7° C. for 15 minutes, the rest of diisopropyl ether was added dropwise, and the mixture was stirred at 45.8 to 49.7° C. for 15 minutes. The mixture was cooled to 15° C., and stirred at 6.5 to 15.0° C. for 30 minutes. The deposited crystal was collected by filtration, and the collected crystal was washed with 6.93 L of acetone and 13.9 L of diisopropyl ether, to obtain 7.41 kg of wet crystal. The wet crystal obtained was dried under reduced pressure at a setting temperature of 65.0° C. for about 20 hours to obtain 6.47 kg of bis(acetato-O)-[6,7-difluoro-1-(2-fluoroethyl)-8-methoxy-4-oxo-1,4-dihydroquinoline-3-carboxylato-$O^3,O^4$]boron (yield: 90.3%).

Elemental Analysis Value (%): as $C_{17}H_{15}BF_3NO_8$.
Calcd.: C, 47.58; H, 3.52; N, 3.26.
Measured: C, 47.41; H, 3.41; N, 3.20.
$^1$H-NMR (CDCl$_3$, 400 MHz) δ: 2.04 (6H, s), 4.21 (3H, d, J=2.9 Hz), 4.88 (2H, dt, J=47.0, 4.4 Hz), 5.21 (2H, dt, J=24.9, 3.9 Hz), 8.17 (1H, t, J=8.8 Hz), 9.10 (1H, s).
ESI MS (positive) m/z: 430 (M+H)+.

Reference Example 2

Production of 7-[(3S,4S)-3-{(cyclopropylamino) methyl}-4-fluoropyrolidin-1-yl]-6-fluoro-1-(2-fluoroethyl)-8-methoxy-4-oxo-1,4-dihydroquinoline-3-carboxylic acid hydrochloride A mixed liquid of 3.56 kg (15.4 mol) of (3R,4S)-3-cyclopropylaminomethyl-4-fluoropyrolidine, 11.7 L (84.2 mol) of triethylamine, and 30.0 L of dimethylsulfoxide was stirred at 23.0 to 26.3° C. for 15 minutes under a nitrogen atmosphere. 6.00 kg (14.0 mol) of bis(acetato-O)-[6,7-difluoro-1-(2-fluoroethyl)-8-methoxy-4-oxo-1,4-dihydroquinoline-3-carboxylato-$O^3,O^4$]boron was added to the mixed liquid at 23.7 to 26.3° C. to obtain a reaction liquid. The reaction liquid was stirred at 23.7 to 26.3° C. for 2 hours. To the reaction liquid, 120 L of ethyl acetate was added, 120 L of water was added, a solution of 960 g (amount corresponding to 2 mol/L) of sodium hydroxide and 12.0 L of water was added, and the mixture was stirred for 5 minutes. After that, an aqueous layer was separated. To the aqueous layer, 120 L of ethyl acetate was added, and the mixture was stirred for 5 minutes. After that, an ethyl acetate layer was separated. The portions of the ethyl acetate layer were combined, 120 L of water was added, and the mixture was stirred for 5 minutes and allowed to stand. After that, an aqueous layer was removed. The ethyl acetate layer was distilled off under reduced pressure. The resultant residue was dissolved in 60.0 L of 2-propanol, and allowed to stand at room temperature overnight. A solution of 5.24 L (62.9 mol) of hydrochloric acid and 26.2 L (amount corresponding to 2 mol/L) of water was added to the solution, and the mixture was stirred at 28.2 to 30.0° C. for 30 minutes. The mixture was heated at an external temperature of 55.0° C. After dissolution (Dissolution was confirmed at 47.1° C.), the mixture was cooled, resulting in crystallization. The mixture was stirred at 39.9 to 41.0° C. for 30 minutes, cooled (guide: to 20.0° C. at a setting temperature of 7.0° C., and to 20.0° C. or lower at −10.0° C.), and stirred at 2.2 to 10.0° C. for 1 hour. The deposited crystal was collected by filtration, and washed with 60 L of 2-propanol to obtain 9.57 kg of crude wet crystal of 7-{(3S,4S)-3-[(cyclopropylamino) methyl]-4-fluoropyrolidin-1-yl}-6-fluoro-1-(2-fluoroethyl)-8-methoxy-4-oxo-1,4-dihydroquinoline-3-carboxylic acid hydrochloride.

Reference Example 3

Method of Producing 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride (A-type crystal, Compound 1)

9.57 kg of crude wet crystal of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride was added to a mixed liquid of 60 L of ethanol and 10.8 L of purified water, and dissolved by heating. This solution was passed through a filter, and washed with a mixed liquid of 24.0 L of ethanol and 1.20 L of purified water. When dissolution was confirmed, 96.0 L of heated ethanol (99.5) was added at 71.2 to 72.6° C. The solution was cooled (hot water setting temperature: 60.0° C.). After crystallization was confirmed (crystallization temperature: 61.5° C.), the solution was stirred at 59.4 to 61.5° C. for 30 minutes. The solution was stepwise cooled (to 50.0° C. at a hot water setting temperature of 40.0° C., to 40.0° C. at a hot water setting temperature of 30.0° C., to 30.0° C. at a hot water setting temperature of 20.0° C., to 20.0° C. at a setting temperature of 7.0° C., and to 15.0° C. at a setting temperature of −10.0° C., and then left to stand), and stirred at 4.8 to 10.0° C. for 1 hour. The deposited crystal was collected by filtration, and washed with 30.0 L of ethanol to obtain 5.25 kg of wet crystal of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride. The wet crystal obtained was dried under reduced pressure at a setting temperature of 50.0° C. for about 13 hours to obtain 4.83 kg of Compound 1 (yield: 72.6%).

Figure 1:
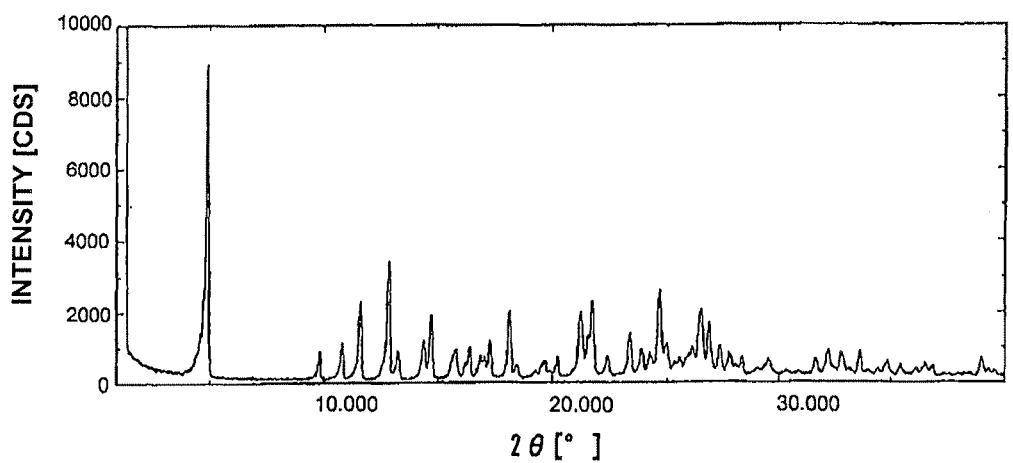
FIG. 1 is an X-ray powder diffraction pattern of 7-[(3S, 4S)-3-{(cyclopropylamino)methyl}-4-fluoropyrolidin-1- yl}-6-fluoro-1-(2-fluoroethyl)-8-methoxy-4-oxo-1,4-dihydroquinoline-3-carboxylic acid hydrochloride (A-type crystal).

FIG. 1 shows a result of X-ray powder diffraction of Compound 1 based on WO2013/069297. As understood from FIG. 1, peaks are found at 4.9°, 10.8°, 12.9°, 18.2°, 21.7°, 24.7°, and 26.4°, and characteristic peaks are confirmed at 10.8°, 12.9°, and 24.7°.

Elementary Analysis Value (%): as $C_{21}H_{24}F_3N_3O_4HCl$.
Calcd.: C, 53.00; H, 5.30; N, 8.83.
Measured: C, 53.04; H, 5.18; N, 8.83.
$^1$H NMR (DMSO-$d_6$, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, brs), 15.11 (1H, brs).
ESI MS (positive) m/z: 440 (M+H)+.

Reference Example 4

7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride hydrate (B-type crystal, Compound 2)

30.0 g (63.0 mmol) of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride obtained in Reference Example 2 was added to a mixed solvent of 600 mL of 2-propanol and 90.0 mL of water, and dissolved by heating (inner temperature: 72° C.) The solution was cooled, crystallization was confirmed (inner temperature: 49° C.), and then the solution was stirred at a temperature near the crystallization temperature for 5 minutes (inner temperature: 48 to 49° C.). The solution was heated until the inner temperature was increased from the crystallization temperature by about 10° C., and then stirred at the temperature for 30 minutes (inner temperature: 48 to 60° C.). The solution was gradually cooled (at about 1° C./min), and stirred at 10° C. or lower for 1 hour (inner temperature: 2 to 10° C.). The deposited crystal was collected by filtration, and washed with a mixed solvent of 143 mL of 2-propanol and 7.5 mL of water to obtain 34.5 g of 7-{(3S,4S)-3-[(cyclopropylamino)methyl]-4-fluoropyrolidin-1-yl}-6-fluoro-1-(2-fluoroethyl)-8-methoxy-4-oxo-1,4-dihydroquinoline-3-carboxylic acid hydrochloride hydrate (B-type crystal) as a white powder.

FIG. 2 shows a result of X-ray powder diffraction of Compound 2 based on WO2013/069297. As understood from FIG. 2, peaks are found at 4.8°, 9.4°, 17.7°, 22.8°, 25.8°, and 27.0°, and characteristic peaks are confirmed at 9.4° and 17.7°.

$^1$H NMR (DMSO-$d_6$, 400 MHz) δ (ppm): 0.77-0.81 (2H, m), 0.98-1.00 (2H, m), 2.79-2.93 (2H, m), 3.22 (1H, dd, J=8.4, 12.2 Hz), 3.58 (3H, s), 3.65-3.81 (3H, m), 4.13 (1H, dd, J=13.2, 42.1 Hz), 4.81-4.97 (2H, m), 5.15 (1H, dd, J=15.7, 32.8 Hz), 5.55 (1H, d, J=53.8 Hz), 7.79 (1H, dd, J=2.4, 13.2 Hz), 8.85 (s, 1H), 9.56 (2H, brs), 15.07 (1H, brs).

Example 1

In accordance with formulation in Table 1, Compound 1, L-glutamic acid hydrochloride which was crushed using a pestle and a mortar and passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation number: 3 min$^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with an R plane having a curvature radius of 10 mm) so that the mass was 250 mg and the thickness was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION), forming an aqueous coating.

Example 2

The same operation as in Example 1 was performed except that L-(+)tartaric acid was used instead of L-glutamic acid hydrochloride.

Example 3

The same operation as in Example 1 was performed except that citric acid anhydride was used instead of L-glutamic acid hydrochloride.

Example 4

The same operation as in Example 1 was performed except that DL-malic acid was used instead of L-glutamic acid hydrochloride.

Example 5

The same operation as in Example 1 was performed except that fumaric acid was used instead of L-glutamic acid hydrochloride.

Example 6

The same operation as in Example 1 was performed except that monobasic sodium citrate was used instead of L-glutamic acid hydrochloride.

Comparative Example 1

The same operation as in Example 1 was performed except that dibasic sodium citrate was used instead of L-glutamic acid hydrochloride.

Comparative Example 2

The same operation as in Example 1 was performed except that sodium citrate was used instead of L-glutamic acid hydrochloride.

Comparative Example 3

In accordance with formulation in Table 1, Compound 1, and crystalline cellulose which was crushed using a pestle and a mortar and passed through a sieve with an opening of 212 μm were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation number: 3 $min^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with an R plane having a curvature radius of 10 mm) so that the mass was 250 mg and the thickness was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION), forming an aqueous coating.

Example 7

In accordance with formulation in Table 2, Compound 1, alginic acid which was crushed using a pestle and a mortar and passed through a sieve with an opening of 212 μm, monobasic sodium citrate passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation number: 3 $min^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 8.5 mm, punch with an R plane having a curvature radius of 10 mm) so that the mass was 250 mg and the thickness was 4.2 mm, to obtain an uncoated tablet. The uncoated tablet was coated with a mixture of hypromellose, titanium oxide, and polyethylene glycol 400 using a Hicoater (HCT-MINI manufactured by FREUND CORPORATION), forming an aqueous coating.

Example 8

The same operation as in Example 7 was performed except that L-aspartic acid was used instead of alginic acid.

TABLE 1

| | COMPONENT | EXAMPLE 1 | EXAMPLE 2 | EXAMPLE 3 | EXAMPLE 4 | EXAMPLE 5 | EXAMPLE 6 | COMPARATIVE EXAMPLE 1 | COMPARATIVE EXAMPLE 2 | COMPARATIVE EXAMPLE 3 |
|---|---|---|---|---|---|---|---|---|---|---|
| UNCOATED TABLET | COMPOUND 1 | 108.3 | 108.3 | 108.3 | 108.3 | 108.3 | 108.3 | 108.3 | 108.3 | 108.3 |
| | L-GLUTAMIC ACID HYDROCHLORIDE | 21.6 | — | — | — | — | — | — | — | — |
| | L-(+)TARTARIC ACID | — | 21.6 | — | — | — | — | — | — | — |
| | ANHYDROUS CITRIC ACID | — | — | 21.6 | — | — | — | — | — | — |
| | DL-MALIC ACID | — | — | — | 21.6 | — | — | — | — | — |
| | FUMARIC ACID | — | — | — | — | 21.6 | — | — | — | — |
| | MONOBASIC SODIUM CITRATE | — | — | — | — | — | 21.6 | — | — | — |
| | DIBASIC SODIUM CITRATE | — | — | — | — | — | — | 21.6 | — | — |
| | SODIUM CITRATE | — | — | — | — | — | — | — | 21.6 | — |
| | CRYSTALLINE CELLULOSE | 17.85 | 17.85 | 17.85 | 17.85 | 17.85 | 17.85 | 17.85 | 17.85 | 39.45 |
| | MAGNESIUM STEARATE | 2.25 | 2.25 | 2.25 | 2.25 | 2.25 | 2.25 | 2.25 | 2.25 | 2.25 |
| | SUBTOTAL (mg) | 150 | 150 | 150 | 150 | 150 | 150 | 150 | 150 | 150 |
| | CRYSTALLINE CELLULOSE* | 73.75 | 73.75 | 73.75 | 73.75 | 73.75 | 73.75 | 73.75 | 73.75 | 73.2 |
| | LOW SUBSTITUTED HYDROXYPROPYLCELLULOSE | 25 | 25 | 25 | 25 | 25 | 25 | 25 | 25 | 25 |
| | MAGNESIUM STEARATE* | 1.25 | 1.25 | 1.25 | 1.25 | 1.25 | 1.25 | 1.25 | 1.25 | 1.25 |
| | SUBTOTAL (mg) | 250 | 250 | 250 | 250 | 250 | 250 | 250 | 250 | 250 |
| COATING | HYPROMELLOSE | 5 | 5 | 5 | 5 | 5 | 5 | 5 | 5 | 5 |
| | TITANIUM OXIDE | 2.5 | 2.5 | 2.5 | 2.5 | 2.5 | 2.5 | 2.5 | 2.5 | 2.5 |
| | POLYETHYLENE GLYCOL 400 | 0.5 | 0.5 | 0.5 | 0.5 | 0.5 | 0.5 | 0.5 | 0.5 | 0.5 |
| | TOTAL (mg) | 258 | 258 | 258 | 258 | 258 | 258 | 258 | 258 | 258 |

*Added after granulation

Example 9

The same operation as in Example 7 was performed except that L-glutamic acid was used instead of alginic acid.

TABLE 2

| | COMPONENT | EXAMPLE 7 | 8 | 9 | 6 |
|---|---|---|---|---|---|
| UNCOATED TABLET | COMPOUND 1 | 108.3 | 108.3 | 108.3 | 108.3 |
| | ALGINIC ACID | 7.2 | — | — | — |
| | L-ASPARTIC ACID | — | 7.2 | — | — |
| | L-GLUTAMIC ACID | — | — | 7.2 | — |
| | MONOBASIC SODIUM CITRATE | 21.6 | 21.6 | 21.6 | 21.6 |
| | CRYSTALLINE CELLULOSE | 10.65 | 10.65 | 10.65 | 17.85 |
| | MAGNESIUM STEARATE | 2.25 | 2.25 | 2.25 | 2.25 |
| | SUBTOTAL (mg) | 150 | 150 | 150 | 150 |
| | CRYSTALLINE CELLULOSE* | 73.75 | 73.75 | 73.75 | 73.75 |
| | LOW SUBSTITUTED HYDROXYPROPYLCELLULOSE | 25 | 25 | 25 | 25 |
| | MAGNESIUM STEARATE* | 1.25 | 1.25 | 1.25 | 1.25 |
| | SUBTOTAL (mg) | 250 | 250 | 250 | 250 |
| COATING | HYPROMELLOSE | 5 | 5 | 5 | 5 |
| | TITANIUM OXIDE | 2.5 | 2.5 | 2.5 | 2.5 |
| | POLYETHYLENE GLYCOL 400 | 0.5 | 0.5 | 0.5 | 0.5 |
| | TOTAL (mg) | 258 | 258 | 258 | 258 |

*Added after granulation

Example 10

In accordance with formulation in Table 3, Compound 1, alginic acid and monobasic sodium citrate which were passed through a sieve with an opening of 212 μm, and crystalline cellulose were mixed in a polyethylene bag for 3 minutes. To the mixture, magnesium stearate was added, and the mixture was mixed in the polyethylene bag for 1 minute. The mixture was compression-molded with a ROLLER COMPACTOR (TF-MINI, manufactured by FREUND CORPORATION, roll pressure: 70 kgf, roll rotation number: 3 min$^{-1}$), and subjected to size adjustment using a ROLL GRANULATOR (GRN-T-54-S, manufactured by NIPPON GRANULATOR CO., LTD.) to obtain a granulated substance (using rolls with four pitch widths of 6 mm, 2 mm, 1.2 mm, and 0.6 mm). The resulting granulated substance was passed through a sieve with an opening of 850 μm, to obtain a sieved product as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 7.5 mm, punch with an R plane having a curvature radius of 9 mm) so that the mass was 190 mg and the thickness was 3.9 mm, to obtain an uncoated tablet. The uncoated tablet was coated with a mixture of hypromellose, titanium oxide, polyethylene glycol 400, and yellow ferric oxide using a Hicoater (HCT-MINI manufactured by FREUND CORPORATION), forming an aqueous coating.

Example 11

In accordance with formulation in Table 3, Compound 2, alginic acid passed through a sieve with an opening of 212 μm, monobasic sodium citrate, and crystalline cellulose were uniformly mixed using a pestle and a mortar. To the mixture, magnesium stearate was added, and the mixture was mixed using a pestle and a mortar. The mixture was pressed into a tablet using a tableting machine (HT-AP-18SS-II, manufactured by HATA TEKKOSHO CO., LTD.), a mortar with a diameter of 7.5 mm, and a punch with an R plane having a curvature radius of 9 mm so that the mass was 190 mg. The tablet was crushed using a pestle and a mortar to obtain a granulated substance as main drug granules. The main drug granules, crystalline cellulose, and low substituted hydroxypropylcellulose were then mixed for 3 minutes in a polyethylene bag. To the mixture, magnesium stearate was added, and the mixture was mixed in the polyethylene bag for 1 minute. The mixture was pressed into a tablet using a tableting machine (HT-AP-18SS-II, manufactured by HATA TEKKOSHO CO., LTD., diameter of mortar: 7.5 mm, punch with an R plane having a curvature radius of 9 mm) so that the mass was 190 mg and the thickness was 3.9 mm, to obtain an uncoated tablet. The uncoated tablet was coated with a mixture of hypromellose, titanium oxide, polyethylene glycol 400, and yellow ferric oxide using a Hicoater (HCT-MINI manufactured by FREUND CORPORATION), forming an aqueous coating.

TABLE 3

| COMPONENT | EXAMPLE 10 | EXAMPLE 11 |
|---|---|---|
| COMPOUND 1 (A-TYPE CRYSTAL) | 81.2 | — |
| COMPOUND 2 (B-TYPE CRYSTAL) | — | 81.2 |
| ALGINIC ACID | 5.4 | 5.4 |
| MONOBASIC SODIUM CITRATE | 16.2 | 16.2 |
| CRYSTALLINE CELLULOSE | 8 | 8 |
| MAGNESIUM STEARATE | 1.7 | 1.7 |
| SUBTOTAL (mg) | 112.5 | 112.5 |
| CRYSTALLINE CELLULOSE* | 56.5 | 56.5 |
| LOW SUBSTITUTED HYDROXYPROPYLCELLULOSE | 20 | 20 |
| MAGNESIUM STEARATE* | 1 | 1 |
| SUBTOTAL (mg) | 190 | 190 |
| HYPROMELLOSE | 3.6 | 3.6 |
| TITANIUM OXIDE | 1.96 | 1.96 |

TABLE 3-continued

| COMPONENT | EXAMPLE 10 | EXAMPLE 11 |
|---|---|---|
| POLYETHYLENE GLYCOL 400 | 0.36 | 0.36 |
| YELLOW FERRIC OXIDE | 0.08 | 0.08 |
| TOTAL (mg) | 196 | 196 |

*Added after granulation

Test Example 1

50 mg of each of the acidic substances used in Examples 1 to 11, dibasic sodium citrate used in Comparative Example 1, and sodium citrate used in Comparative Example 2 was weighed, and dissolved or suspended in 1,950 µL of water, and pH of each obtained liquid (concentration: 2.5%) was measured with a pH meter. Measurement results are shown in Table 4.

TABLE 4

| | ACIDIC SUBSTANCE | pH |
|---|---|---|
| EXAMPLE 1 | L-GLUTAMIC ACID HYDROCHLORIDE | 1.5 |
| EXAMPLE 2 | L-(+)TARTARIC ACID | 1.9 |
| EXAMPLE 3 | ANHYDROUS CITRIC ACID | 2.1 |
| EXAMPLE 4 | DL-MALIC ACID | 2.1 |
| EXAMPLE 5 | FUMARIC ACID | 2.2 |
| EXAMPLES 7, 10 and 11 | ALGINIC ACID | 2.2 |
| EXAMPLE 8 | L-ASPARTIC ACID | 2.8 |
| EXAMPLE 9 | L-GLUTAMIC ACID | 3.0 |
| EXAMPLE 6 | MONOBASIC SODIUM CITRATE | 3.7 |
| COMPARATIVE EXAMPLE 1 | DIBASIC SODIUM CITRATE | 5.1 |
| COMPARATIVE EXAMPLE 2 | SODIUM CITRATE | 8.2 |

Test Example 2

Each of the compositions (tablets) in Examples 2 to 6, and 11, and Comparative Examples 1 to 3 was placed in a glass bottle, and stored in an opened state or a sealed state under conditions of 60° C. and 90% RH for 2 weeks. After the storage, the content of 7-{(3S,4S)-3-aminomethyl-4-fluoro-pyrolidin-1-yl}-6-fluoro-1-(2-fluoroethyl)-8-methoxy-4-oxo-1,4-dihydroquinoline-3-carboxylic acid (Compound 3) and the content of Compound 1 were measured through liquid chromatography, and the content of Compound 3 was represented as a percentage based on the content of Compound 1.

Liquid Chromatography Test Condition

Column: a separation column in which each stainless tube with an inner diameter of 4.6 mm and a length of 150 mm was charged with octadecyl-silylated silica gel of 3 µm for liquid chromatography (GL Sciences Inc., Inertsil ODS-3).

A liquid: a liquid in which 2.16 g of sodium 1-octane-sulfonate was dissolved in diluted phosphoric acid (1→1, 000) in a volume of 1,000 mL.

B liquid: methanol for liquid chromatography

Liquid sending: The mixed ratio of A liquid and B liquid was changed to control the concentration gradient.

Detector: UV absorption spectrophotometer (measurement wavelength: 294 nm)

Retention time of Compound 3 with respect to Compound 1: 0.69

The stability test results of Examples 2 to 6, and 11 and Comparative Examples 1 to 3 are shown in Table 5. In the tablets which contain an acidic substance of pH 4.0 or lower (Examples 2 to 6, and 11), the production of decomposed substance tends to be suppressed as compared with the tablet which contains an acidic substance of pH higher than 4.0 (Comparative Example 1), the tablet which does not contain an acidic substance (Comparative Example 3), and the tablet which contains a basic substance (Comparative Example 2). The stabilization effect is particularly marked in a tablet after storage in a sealed state. The stabilization effect of the tablet which contains an acidic substance having lower pH is higher.

TABLE 5

| | pH OF ACIDIC SUBSTANCE OR BASIC SUBSTANCE ADDED | CONTENT OF COMPOUND 3 (DURING INITIATION) % | CONTENT OF COMPOUND 3 (AFTER STORAGE IN OPENED STATE) % | CONTENT OF COMPOUND 3 (AFTER STORAGE IN SEALED STATE) % |
|---|---|---|---|---|
| EXAMPLE 2 | 1.9 | N.D. | 0.06 | 0.02 |
| EXAMPLE 3 | 2.1 | N.D. | 0.09 | 0.03 |
| EXAMPLE 4 | 2.1 | N.D. | 0.07 | 0.02 |
| EXAMPLE 5 | 2.2 | N.D. | 0.13 | 0.05 |
| EXAMPLE 11* | 2.2 | 0.09 | 0.53 | 0.14 |
| EXAMPLE 6 | 3.7 | N.D. | 0.46 | 0.19 |
| COMPARATIVE EXAMPLE 1 | 5.1 | N.D. | 2.08 | 0.35 |
| COMPARATIVE EXAMPLE 2 | 8.2 | <0.05 | 15.88 | 0.59 |
| COMPARATIVE EXAMPLE 3 | NONE | N.D. | 0.35 | 0.30 |

*In Example 11, Compound 2 (B-type crystal) was used.

Test Example 3

Appearance Observation (Immediately after Production)

The results of appearance observation of the coating tablets obtained in Examples 1 to 9 are shown in Table 6.

TABLE 6

| | ACIDIC SUBSTANCE | pH | SOLUBILITY IN WATER (20° C.) | PRESENCE OR ABSENCE OF MOTTLES |
|---|---|---|---|---|
| EXAMPLE 1 | L-GLUTAMIC ACID HYDROCHLORIDE | 1.5 | 27.5% | ABSENCE |
| EXAMPLE 2 | L-(+)TARTARIC ACID | 1.9 | 58.2% | PRESENCE |
| EXAMPLE 3 | ANHYDROUS CITRIC ACID | 2.1 | 59.2% | PRESENCE |
| EXAMPLE 4 | DL-MALIC ACID | 2.1 | 36.0% | PRESENCE |
| EXAMPLE 5 | FUMARIC ACID | 2.2 | 0.63% | ABSENCE |
| EXAMPLE 6 | MONOBASIC SODIUM CITRATE | 3.7 | 5.4% | ABSENCE |
| EXAMPLE 7 | ALGINIC ACID* | 2.2 | — ** | ABSENCE |
| EXAMPLE 8 | L-ASPARTIC ACID* | 2.8 | 0.4% | ABSENCE |
| EXAMPLE 9 | L-GLUTAMIC ACID* | 3.0 | 0.75% | ABSENCE |

*In Examples 7 to 9, sodium dihydrogen citrate was also used in addition to acidic substances described in Table 5.
** Alginic acid is hardly dissolved in water (Pharmaceutical Excipients Directory 2007).

As seen from Table 6, when an acidic substance having a solubility in water at 20° C. of more than 30% was used, convex mottles confirmed in Examples 2 to 4 were generated on the surface of the tablet. In contrast, when an acidic substance having a solubility in water at 20° C. of 30% or less, such as L-glutamic acid hydrochloride, fumaric acid, monobasic sodium citrate, alginic acid, L-aspartic acid, and L-glutamic acid, was used, a mottle was not confirmed on the surface of the tablet. FIGS. 3 to 11 show photographs of the tablets in Examples 1 to 9 immediately after production. (Example 1: FIG. 3, Example 2: FIG. 4, Example 3: FIG. 5, Example 4: FIG. 6, Example 5: FIG. 7, Example 6: FIG. 8, Example 7: FIG. 9, Example 8: FIG. 10, and Example 9: FIG. 11)

Test Example 4

Appearance Observation (after Storage for 2 Weeks)

Each of the compositions in Examples 1 to 7, 9, and 11 was placed in a glass bottle, and stored in an opened state under conditions of 60° C. and 90% RH for 2 weeks. The results of appearance observation after storage for 2 weeks are shown in Table 7.

TABLE 7

| | ACIDIC SUBSTANCE | pH | APPEARANCE CHANGE |
|---|---|---|---|
| EXAMPLE 1 | L-GLUTAMIC ACID HYDROCHLORIDE | 1.5 | PRESENCE |
| EXAMPLE 2 | L-(+)TARTARIC ACID | 1.9 | PRESENCE |
| EXAMPLE 3 | ANHYDROUS CITRIC ACID | 2.1 | PRESENCE |
| EXAMPLE 4 | DL-MALIC ACID | 2.1 | PRESENCE |
| EXAMPLE 5 | FUMARIC ACID | 2.2 | ABSENCE |
| EXAMPLE 6 | MONOBASIC SODIUM CITRATE | 3.7 | ABSENCE |
| EXAMPLE 7* | ALGINIC ACID | 2.2 | ABSENCE |
| EXAMPLE 9* | L-GLUTAMIC ACID | 3.0 | ABSENCE |
| EXAMPLE 11* | ALGINIC ACID | 2.2 | ABSENCE |

*In Examples 7, 9, and 11, sodium dihydrogen citrate was also used in addition to acidic substances in Table 7.

As seen from Table 7, when an acidic substance of pH lower than 2.2 was used, an appearance was changed after storage under the above-described conditions. In contrast, when an acidic substance of pH 2.2 or higher was used, an appearance was not changed. Therefore, it can be understood that an acidic substance of pH 2.2 or higher is preferably used.

FIGS. 12 to 20 are photographs of the tablets obtained in Examples 1 to 7, 9, and 11 after storage under conditions of 60° C. and 90% RH for 2 weeks. (Example 1: FIG. 12, Example 2: FIG. 13, Example 3: FIG. 14, Example 4: FIG. 15, Example 5: FIG. 16, Example 6: FIG. 17, Example 7: FIG. 18, Example 9: FIG. 19, and Example 11: FIG. 20)

INDUSTRIAL APPLICABILITY

When a solid pharmaceutical composition which contains the compound of the formula (1) or a salt thereof contains a cellulosic excipient, and an acidic substance of pH 4.0 or lower, the solid pharmaceutical composition in which the decomposition of the compound of the formula (1) or salt thereof is suppressed can be provided.

The invention claimed is:
1. A solid pharmaceutical composition comprising:
7-[3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride;
a cellulosic excipient; and
an acidic substance having a pH of 4.0 or lower,
wherein the acidic substance is at least one compound selected from the group consisting of glutamic acid hydrochloride, tartaric acid, citric acid, malic acid, fumaric acid, monobasic sodium citrate, glutamic acid, aspartic acid, and alginic acid.
2. The solid pharmaceutical composition according to claim 1, wherein the acidic substance has a solubility in water at 20° C. of 30% or less.
3. The solid pharmaceutical composition according to claim 1, wherein the acidic substance has a pH of 2.2 or higher and 4.0 or lower.
4. The solid pharmaceutical composition according to claim 1, wherein the acidic substance is at least one compound selected from the group consisting of fumaric acid, monobasic sodium citrate, glutamic acid, aspartic acid, and alginic acid.
5. The solid pharmaceutical composition according to claim 1, wherein the cellulosic excipient is crystalline cellulose.
6. The solid pharmaceutical composition according to claim 1, which is obtained by mixing the 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride, the cellulosic excipient, and the acidic substance to obtain a mixture,
wherein the acidic substance is at least one compound selected from the group consisting of glutamic acid hydrochloride, tartaric acid, citric acid, malic acid, fumaric acid, monobasic sodium citrate, glutamic acid, aspartic acid, and alginic acid, and granulating the mixture through a dry granulation method.

7. A method of producing a solid pharmaceutical composition, comprising:

mixing 7-[(3S,4S)-3-{(cyclopropylamino)methyl}-4-fluoropyrolidin-1-yl]-6-fluoro-1-(2-fluoroethyl)-8-methoxy-4-oxo-1,4-dihydroquinoline-3-carboxylic acid hydrochloride, a cellulosic excipient, and an acidic substance having a pH of 4.0 or lower to obtain a mixture, wherein the acidic substance is at least one compound selected from the group consisting of glutamic acid hydrochloride, tartaric acid, citric acid, malic acid, fumaric acid, monobasic sodium citrate, glutamic acid, aspartic acid, and alginic acid; and granulating the mixture through a dry granulation method.

* * * * *